United States Patent [19]
Larock

[11] Patent Number: 5,721,371
[45] Date of Patent: Feb. 24, 1998

[54] SYNTHESIS OF SUBSTITUTED PTEROCARPANS

[75] Inventor: Richard C. Larock, Ames, Iowa

[73] Assignee: Iowa State University Research Foundation, Inc., Ames, Iowa

[21] Appl. No.: 767,794

[22] Filed: Dec. 17, 1996

Related U.S. Application Data

[60] Provisional application No. 60/008,780, Dec. 18, 1995, and 60/019,398, Jun. 7, 1996.

[51] Int. Cl.$^6$ .................................. C07D 311/78
[52] U.S. Cl. .................................. 549/383
[58] Field of Search .................................. 549/383

[56] References Cited

U.S. PATENT DOCUMENTS

| | | | |
|---|---|---|---|
| 4,335,054 | 6/1982 | Blaser et al. | 260/465 |
| 4,429,141 | 1/1984 | Darko et al. | 549/382 |
| 5,314,899 | 5/1994 | Daly et al. | 514/339 |
| 5,399,558 | 3/1995 | Baker et al. | 549/383 |

OTHER PUBLICATIONS

Arcadi, A., et al., "Palladium–catalyzed Preparation of Exo–aryl Derivatives of the Norbornane Skeleton", *Journal of Organometalic Chemistry*, 368, pp. 249–256, (1989).
Arcadi, A., et al., "Palladium–catalyzed Reaction of 2-Hydroxyaryl and Hydroxyherteroaryl Halides with 1-Alkynes: An Improved Route to the Benzo[b]furan Ring System.", *Synthesis*, pp. 749–751, (Sep., 1986).
Ariamala, G., et al., "Radical Cyclisation: Synthesis of 4H–furo(3,2–c)–1–benzopyrans", *Tet. Lett.*, 29, pp. 3335–3338, (1988).
Broka, C.A., "Total Synthesis of Epibatidine", *Tet. Lett.*, 34, pp. 3251–3254, (1993).
Brunner, H., et al., "Asymmetric Catalysis. 72. Enantioselective Hydroarylation of Norbornene and Norbornadiene with Palladium(II) Acetate/Phosphine Catalysts", *Synthesis*, pp. 1121–1124, (Dec., 1991).
Castro, C.E., et al., "Indoles, Benzofurans, Phthalides, and Tolanes via Copper(I) Acetylides", *J. Org. Chem.*, 31, pp. 4071–4078, (1966).
Clayton, S.C., et al., "A Total Synthesis of (±)–Epibatidine", *Tet. Lett.*, 34, pp. 7493–7496, (1993).
Corey, E.J., et al., "Stereocontrolled Total Synthesis (+)– and (−)–Epibatidine", *J. Org. Chem.*, 58, pp.3600–3602, (1993).
Dean, F.M., "Isoflavones and Isoflavanones", In: *Naturally Occuring Oxygen Ring Compounds*, Butterworths, London, pp. 366–387, (1963).
Engler, T.A., et al., "Asymmetric Induction in Reactions of Styrenes with 1,4–Benzoquinones Utilizing Chiral Ti(IV) Complexes", *J. Am. Chem. Soc.*, 113, pp. 5068–5070, (1991).
Engler, T.A., et al., "Synthetic Pterocarpans with Anti–HIV Activity", *Bioorganic & Medicinal Chemistry Letters*, 3, pp. 1229–1232, (1993).

Engler, T.A., et al., "Formal 2 + 2 and 3 + 2 Cycloaddition Reactions of 2H–Chromenes with 2–Alkoxy–1,4–benzoquinones: Regioselective Synthesis of Substituted Pterocarpans", *J. Org. Chem.*, 55, pp. 1248–1254, (1990).
Fletcher, S.R., et al., "The Synthesis of (+)– and (−)–Epibatidine", *J. Chem. Soc., Chem. Commun.*, 15, pp. 1216–1218, (1993).
Gnanamanickam, S.S., et al., "Selective Toxicity of Wyerone and Other Phytoalexins to Gram–positive Bacteria", *Phytochemistry*, 20, pp. 997–1000, (1981).
Horino, H., et al., "A New Route to Chromanocoumarans. Synthesis of (±)–Pterocarpin", *J. Chem. Soc., Chem. Commun.*, 13, pp. 500–501, (1976).
Huang, D.F., et al., "A Versatile Total Synthesis of Epibatidine and Analogs", *Tet. Lett.*, 34, pp. 4477–4480, (1993).
Iinuma, M., et al., "Flavonoid Compounds in Roots of *Sophora tetraptera*", *Phytochemistry*, 39, pp. 667–672, (1995).
Iinuma, M., et al., "Flavonoids in Roots of *Sophora prostrata*", *Phytochemistry*, 38, pp. 539–543, (1995).
Kojima, R., et al., "Antitumor Activity of Leguminosae Plants Constituents. I. Antitumor Activity of Constituents of *Sophora subprostrata*", *Chem. Pharm. Bull.*, 18, pp. 2555–2563, (1970).
Korte, D.E., et al., "Synthesis of Isocoumarins, Dihydroisocoumarins, and Isoquinolones via Allylnickel Halide and Olefin–Palladium Complexes", *J. Org. Chem.*, 42, pp. 1329–1336, (1977).
Kundu, N.G., et al., "Palladium–Catalysed Heteroannulation of Acetylenic Compounds: a Facile Method for the Synthesis of Benzofurans", *J. Chem. Soc., Chem. Commun.*, 1, pp. 41–42, (1992).
Larock, R.C., et al., "Palladium–Catalyzed Annulation of 1,4–Dienes Using Ortho–Functionally–Substituted Aryl Halides", *J. Org. Chem.*, 58, pp. 4509–4512, (1993).

(List continued on next page.)

*Primary Examiner*—Amelia Owens
*Attorney, Agent, or Firm*—Schwegman, Lundberg, Woessner & Kluth, P.A.

[57] ABSTRACT

The present invention provides a method of synthesizing compounds of formula (I):

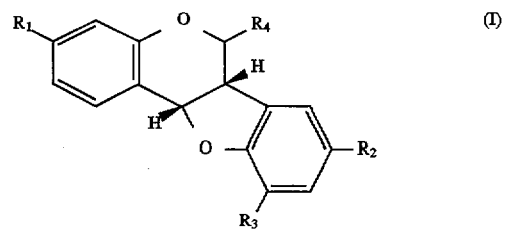

wherein $R_1$ and $R_3$ are independently H or $(C_1–C_4)$alkyl—O—;
$R_2$ is $R_5C(O)$— where $R_5$ is $(C_1–C_4)$alkyl or H; and
$R_4$ is H, $(C_1–C_4)$alkyl or $(C_5–C_7)$aryl optionally substituted with $(C_1–C_4)$alkyl or halo.

16 Claims, No Drawings

OTHER PUBLICATIONS

Larock, R.C., et al., "Palladium–Catalyzed Heteroannulation of 1,3–Dienes by Functionally Substituted Aryl Halides", *J. Org. Chem.*, 55, pp. 3447–3450, (1990).

Larock, R.C., et al., "Regioselective, Palladium–Catalyzed Hetero– and Carboannulation of 1,2–Dienes Using Functionally Substituted Aryl Halides", *J. Org. Chem.*, 56, pp. 2615–2617, (1991).

Larock, R.C., et al., "Synthesis of Aromatic Heterocycles via Palladium–Catalyzed Annulation of Internal Alkynes", *J. Org. Chem.*, 60, pp. 3270–3271, (1995).

Larock, R.C., et al., "Synthesis of Homoallylic Alcohols via Organometallic Ring Opening of Vinylic Oxetanes", *Synlett*, pp. 341–343, (Jun., 1990).

Larock, R.C., "New Applications of Organopalladium Compounds in Organic Synthesis", *Pure & Appl. Chem.*, 62, pp. 653–660., (1990).

Larock, R.C., et al., "Palladium–Catalysed Intermolecular Arylation and Alkenylation of Bicyclic Alkenes", *J. Chem. Soc., Chem. Commun.*, 18, pp. 1368–1370, (1989).

Larock, R.C., et al., "Palladium–Catalyzed Annulation of Oxygen–Substituted 1,3–Dienes", *Synlett*, pp. 465–466, (May, 1995).

Larock, R.C., et al., "Synthesis of Indoles via Palladium–Catalyzed Heteroannulation of Internal Alkynes", *J. Am. Chem. Soc.*, 113, pp. 6689–6690 (1991).

Larock, R.C., et al., *Chemical Abstracts*, 112, Abstract #98074, (1989).

Maassarani, F., et al., "Controlled Synthesis of Heterocyclic Compounds through Ring Enlargement by Alkyne Insertions into the Pd–C Bonds of Cyclopalladated Amines Followed by Subsequent Ring Closure", *Organometallics*, 6, pp. 2029–2043, (1987).

Maitlis, P.M., et al., "Acetylenes, Cyclobutadienes and Palladium: A Personal View", *J. Organomet. Chem.*, 200, pp. 161–176, (1990).

March, J., *Advanced Organic Chemistry: Reactions, Mechanisms, and Structure*, McGraw–Hill Book Company, New York, p. 21, (1968).

Miki, Y., et al., "Reaction of Chalcone with Phenyliodine (III) Bis(trifluoroacetate) (PIFA): Synthesis of (±)–Homopterocarpin", *Synlett*, pp. 1001–1002, (Dec., 1994).

Mori, M., et al., "Reactions and Synthesis with Organometallic Compounds. 7. Synthesis of Benzolactams by Palladium–Catalyzed Amidation", *J. Org. Chem.*, 43, pp. 1684–1687, (1978).

Nakagawa, M., et al., "Structures of Cabenegrins A–I and A–II, Potent Anti–Snake Venoms", *Tet. Lett.*, 23, pp. 3855–3858, (1982).

Nakanishi, K., "Recent Studies on Bioactive Compounds from Plants", *J. Nat. Prod.*, 45, pp. 15–26, (1982).

Narkhede, D.D., et al., "Total Synthesis of (±)–Leiocarpin and (±)–Isohemileiocarpin", *Tetrahedron*, 46, pp. 2031–2034, (1990).

Perrin, D.R., et al., "The Antifungal Activity of Pterocarpans towards *Monilinia fructicola*", *Phytochemistry*, 8, pp. 971–978, (1969).

Sakamoto, T., et al., "Condensed Heteroaromatic Ring Systems. XV. Synthesis of Pyranopyridinones from Halopyridinecarbonitriles", *Chem. Pharm. Bull.*, 36, pp. 1890–1894, (1988).

Sakamoto, T., et al., "Condensed Heteroaromatic Ring Systems. VIII. Synthesis of 3–Substituted Isocoumarins from Halobenzoic Acid Derivatives", *Chem. Pharm. Bull.*, 34, pp. 2754–2759, (1986).

Schore, N.E., "Transition–metal–mediated Cycloaddition Reactions of Alkynes in Organic Synthesis", *Chem Rev.*, 88, pp. 1081–1119, (1988).

Spande, T.F., et al., "Epibatidine: A Novel (Chloropyridyl)azabicycloheptane with Potent Analgesic Activity from an Ecuadoran Poison Frog", *J. Am. Chem. Soc.*, 114, pp. 3475–3478, (1992).

Tao, W., et al., "Alkyne Reactions with Arylpalladuim Compounds", *Organometallics*, 8, pp. 2550–2559, (1989).

Thornber, C.W., "Isosterism and Molecular Modification in Drug Design", *Chemical Society Review*, 8, pp. 563–580, (1979).

VanEtten, H.D., "Antifungal Activity of Pterocarpans and Other Selected Isoflavonoids" *Phytochemistry*, 15, pp. 655–659 (1976).

Wade, L.G., Jr., *Organic Chemistry*, Prentice–Hall, Inc., Englewood Cliffs, New Jersey, p. 349, (1987).

Wagner, R.B., et al., *Synthetic Organic Chemistry*, John Wiley & Sons, Inc., New York, p. 655, (1953).

SYNTHESIS OF SUBSTITUTED PTEROCARPANS

This application claims the benefit of U.S. Provisional Application No. 60/008,780, filed on Dec. 18, 1995, and of U.S. Provisional Application No. 60/019,398, filed on Jun. 7, 1996.

BACKGROUND OF THE INVENTION

Phytoalexins are antimicrobial compounds produced by plants in response to stress. It has been suggested that phytoalexins are crucial compounds in plant disease resistance. A large class of isoflavonoid phytoalexins possess a substituted pterocarpan ring system (Dean, F. M. in "The Total Synthesis of Naturally Occurring Oxygen Ring Compounds", ApSimon, J., ed., Wiley-Interscience: New York, 1973, p. 467; Wong, E. in "Fortschritte der Chemie Organischer Naturstoffe", Springer Verlag: Vienna and New York, 1970, Vol. 27, p. 25). Coumestan is the name of the fundamental ring system characteristic of a small, well-defined group of natural products related to the isoflavones.

Representative natural benzopyrans are tetrapterol B from sophora tetragreta (Linuma et al., *Phytochemistry*, 1995, 39, 667) and prostratol D from sophora prostrata, a deciduous shrub used as a folk medicine for antipyretic and respiratory diseases (Linuma et al., *Phytochemistry*, 1995, 38,539). Pterocarpans have also been reported to possess antifungal (Perrin et at., *Phytochemistry*, 1969, 8, 971; Van Etten, H. D., *Phytochemistry*, 1976, 15, 655; Nakanishi, K. J., *Nat. Prod.*, 1982, 45, 15), antibacterial (Gnanamanickam et al., *Phytochemistry*, 1981, 20, 997), antiyeast (Perrin et al., *Phytochemistry*, 1969, 8, 971) and antitumor (Kojima et al., *Chem. Pharm. Bull.*, 1970, 18, 2555) activity, as well as being potent antidotes for snake venom (Nakagawa et at., *Tetrahedron Lett.*, 1982, 23, 3855). Recently, oxygenated pterocarpans have been reported to possess anti-HIV activity (Engler et al., *J. Org. Chem.*, 1990, 55, 1248; Engler et al., *J. Am. Chem. Soc.*, 1991, 113, 5068; Engler et at., *Bioorg. Med. Lett*, 1993, 3, 1229).

Methods for the synthesis of pterocarpans have received considerable attention recently. Miki developed an acid-catalyzed approach to the synthesis of homopterocarpin isolated from pterocarpus santalinus (Miki et al., Synlett, 1994, 1001). Treatment of 1,3-bis(2'-benzyloxy-4'-methoxyphenyl)-propen-1-one with phenyliodine(III) bis(trifluoroacetate) (PIFA) gave a rearrangement product, 1,2-bis(2'-benzyloxy-4'-methoxyphenyl)-3,3-dimethoxypropan-1-one, which was converted into homopterocarpin.

An interesting, but tedious, radical cyclization route to 4H-furo[3,2-c]-1-benzopyrans from 2H-benzopyran was developed by Balasubramanian (Ariamala et al., *Tetrahedron Lett*, 1988, 27, 3335). In this procedure, the 2H-benzopyran upon treatment with N-bromosuccinimide in the presence of propargyl alcohol gave rise to 3,4-dihydro-3-bromo-4-(prop-2-ynyloxy)-2H-1-benzopyran. Radical cyclization of homopterocarpin gave 2,3,3a,9b-tetrahydro-3-methylene-4H-furo[3,3-c]-1-benzopyran. Oxidation of 2,3,3a,9b-tetrahydro-3-methylene-4H furo[3,3-c]-1-benzopyran with osmium tetroxide, followed by sodium periodate, furnished, 3a,9b-dihydro-4H-furo[3,3-c]-1-benzopyran-3(2H)-one, a potential intermediate for the synthesis of pterocarpans.

Recently, Engler demonstrated that 2H-chromenes can undergo 2+2 cycloaddition reactions to give substituted pterocarpans regioselectively, thus providing an efficient route to certain types of pterocarpans. For example, the titanium(IV)-catalyzed reaction of chromene and 2-methoxy-1,4-benzoquinone stereoselectively yields the oxygenated pterocarpan (Engler et al., *J. Org. Chem.*, 1990, 55, 1248).

Despite the different and distinct methodologies present in the literature for the synthesis of pterocarpans, the most widely used approach by far has been the organomercury approach (Hofino et al., *J. Chem. Soc. Chem. Commun.*, 1976, 500). In this process, pterocarpin and other chromanacoumarans are synthesized in one step by the reaction of 2H-chromens with o-chloromercuriophenols in the presence of lithium chloropalladite. Lelocarpin has also been synthesized by Heck arylation of the bischromene, using 2-chloromercurio-4,5-methylenedioxyphenol (Narkhede et al., *Tetrahedron*, 1990, 46, 2031. Unfortunately, this method requires stoichiometric amounts of a toxic organomercury reagent and stoichiometric amounts of expensive palladium reagents.

A number of groups have recently reported the successful synthesis of fused heterocyclic ring systems employing transition metal catalysis. For example, Larock et al. (*J. Org. Chem.*, 1990, 55, 3447;*Synlett* 465 (1995)), reported that the palladium-catalyzed annulation of 1,3-dienes, such as 18, by aryl halides 19 bearing an oxygen-heteroatom in the ortho position affords heterocycles such as 20.

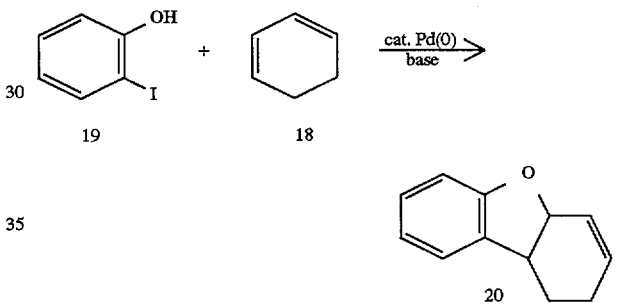

Annulation of vinylic cyclopropanes (Larock et at., *Synlett.*, 341 (1990)); allenes (*J. Org. Chem.*, 56:2615 (1991)); 1,4-dienes (*J. Org. Chem.* 58:4509 (1993)); and alkynes (*J. Org. Chem* 60:3270 (1995)) has also been reported using compound 19.

In view of the importance of pterocarpan formation in organic synthesis and the limitations of currently available methodology, a need exists for synthetic methods which proceed under relatively mild conditions, are tolerant of a wide variety of fictional groups, and utilize readily available benzopyrans as starting materials.

SUMMARY OF THE INVENTION

The present invention provides a method of synthesizing a compound of formula (I):

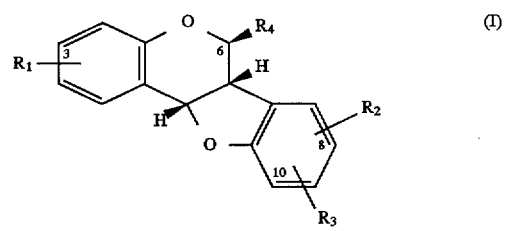

wherein $R_1$, $R_2$, $R_3$ and $R_4$ are independently alkyl, aryl, alkoxy, hydroxy, halogen, nitro, amino, sulfide, sulfoxide or sulfone;

comprising the step of reacting a compound of formula (II):

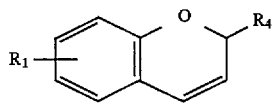

with a compound of formula (III):

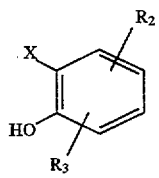

where X is halo (preferably I) or triflate ($CF_3SO_3$); in the presence of a catalytic amount of a Pd catalyst. Preferably, $R_1$ and $R_3$ are independently H, hydroxy, ($C_1$–$C_4$)alkyl or ($C_1$–$C_4$)alkoxy; $R_2$ is $R_5C(O)$— where $R_5$ is ($C_1$–$C_4$)alkyl or H; and $R_4$ is H, hydroxy, ($C_1$–$C_4$)alkyl or ($C_5$–$C_7$)aryl (preferably phenyl) optionally substituted with ($C_1$–$C_4$)alkyl or halo. Preferably, the Pd catalyst is a Pd(0) catalyst or a Pd(II) reagent reducible to Pd(0), such as $Pd(OAc)_2$. The reaction is preferably performed in a suitable organic solvent in the presence of base and a chloride ion source.

The bonds between $R_1$, $R_2$ and $R_3$ indicate that they can occupy any available position on their respective benzo rings. Preferably $R_2$ and $R_3$ are located at the 8 and/or 10 positions of the compound of formula I, and $R_1$ is located at the 3 position.

DETAILED DESCRIPTION OF THE INVENTION

As discussed above, pterocarpans exhibit important antifungal, antibacterial, and anti-HIV activity. The present invention provides a process for the synthesis of pterocarpans involving the Pd(0)-catalyzed heteroannulation of benzopyrans, which are readily available through the Pd(II)-catalyzed cyclization of o-allylic phenols. For example, the starting material 2H-benzopyran 21 is obtained by the oxidative cyclization of 2-allyl phenol (22)

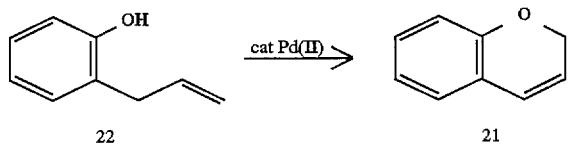

Other convenient methods for preparing 2H-benzofurans such as 21 are known in the art.

In synthesizing compounds of formula (I), the source of the Pd catalyst is generally employed in an amount of about 0.001–20 mol-%, preferably 0.1–10 mol-%, based on the compound of formula 1 and the limiting reagent either II or III (either II or more commonly III is used in excess over the limiting amount of the other reactant). Useful sources of Pd catalyst include Pd(0) catalysts, for example, bis-(dibenzylideneacetone)palladium(0), bis(isonitrile) palladium(0), $Pd(PPh_3)_4$ [tetrakis(triphenylphosphine) palladium(0)]; bis-(cyclohexylisonitrile) palladium(0), bis-(isopropylisonitrile)palladium(0), bis(tert.-butylisonitrile) palladium(0), bis-(p-tolylisonitrile)palladium(0), and bis-(p-methoxyphenyl isonitrile)palladium(0). Other Pd-containing compounds, e.g., Pd(II) compounds, can also be used in the present method. These include $PdCl_2$, palladium(II) carboxylate salts, such as $Pd(OAc)_2$, $PdBr_2$, $Pd(CN)_2$, $Pd(NO_3)_2$, $PdSO_4$ and the like. Other Pd catalysts which can be used in the present method include those disclosed in Blaser et al. (U.S. Pat. No. 4,335,054) at Col. 6, line 5 to Col. 7, line 3.

Bases used in the present process can be inorganic or organic bases, which are adequately soluble in the reaction medium. Representative bases are disclosed at Col. 7, lines 8–65 of the Blaser et al. patent. Inorganic bases for use in the present process include carbonates and bicarbonates, i.e., $Na_2CO_3$, $KHCO_3$, $Li_2CO_3$, $K_2CO_3$, $NaHCO_3$ and the like. Useful organic bases include acetates and amines, such as sodium or potassium acetate, or trialkylamines, such as triethylamine and diisopropyl(ethyl)amine. Preferably, inorganic bases are used. The preferred mole ratio of the base to the compound of formula 1 is about 2–3:1. The base is used in excess (about a ratio 3.5:1) over the limiting reagent (preferably the benzopyran II) and slight excess over the other reagent used (preferably the phenol III, about ratio 1.2).

A source of halide, such as chloride ion, is also preferably used in the present process, in an amount effective to promote the reaction and increase the yield. Organic chloride sources, such as tetra(alkyl)ammonium chlorides, wherein the alkyls can each be about ($C_1$–$C_{12}$)alkyl, are preferred, i.e., (n-Bu)$_4$NCl; or alternatively tetraalkylphosphates. Alkali metal halides such as MX, wherein M is Li, Na, or K and X is Cl, Br or I, can also be used. Preferred in the present method are LiCl or tetra-n-butylammonium chloride (n-Bu$_4$NCl). The halide source is preferably used in an equimolar amount or in only a slight excess over the compound of formula 1 (1.1–1.5 equivalents).

Useful organic solvents include tetrahydrofuran (THF), ethers, glycol ethers, dimethylsulfoxide, dimethylformamide (DMF), acetonitrile, acetamide, dimethylacetamide, and hexamethylphosphoramide, and combinations of these solvents, optionally with minor amounts of water, as compatible.

As used herein, the terms alkyl includes branched, straight chain, cycloalkyl or (cyclcoalkyl)alkyl. The term aryl includes aralkyl, (alkyl)aryl or alkylaralkyl, optionally substituted with 1–2 N, S or nonperoxide O.

As one skilled in the art will appreciate, oxidation of pterocarpans with oxidants such as DDQ yields coumestans (Ferreira et al., J. Chem. Soc. Perkin I, 1974, 2429). Thus, the methods of the present invention may be used to synthesize comestans, and such methods are considered within the scope of the invention.

The following variables were examined to determine preferred reactions conditions: base, concentration, reactant ratio and temperature on the armulation of 2H-benzopyrans. DMF was used as the solvent, $Pd(OAc)_2$ as the catalyst and n-Bu$_4$NCl as the chloride source (scheme 1). All yields were determined by $^1H$ NMR spectroscopy utilizing toluene as an internal reference.

Scheme 1

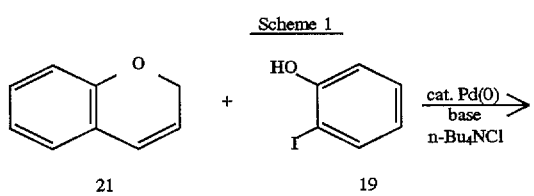

-continued
Scheme 1

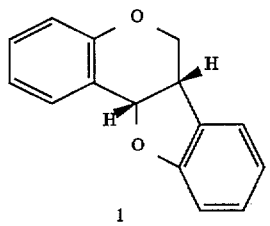

1

With regard to temperature, the results in Table 1 generally indicate that a lower temperature and longer time are detrimental to reaction yield (entry 1). When the reaction was run at 100° C., it proceeded readily, and in 3 days gave a 52% yield of pterocarpan (entry 1).

TABLE 1

Effect of Temperature

| Entry | Base | Time (h) Temp. (°C.) | Volume (ml) | Ratio 21:19 | % Yield 1 |
|---|---|---|---|---|---|
| 1 | NaHCO$_3$ | 72,100 | 5 | 3:1 | 52 |
| 2 | NaHCO$_3$ | 120,80 | 5 | 3:1 | 32 |

The effect of concentration on this reaction was studied. The results are summarized in Table 2, which indicate that the more dilute solution, such as 10 ml for a 0.5 mmol scale, reduces the yield of annulation product. Preferably, five ml of solvent is used for a 0.5 mmole scale.

TABLE 2

Effect of Concentration

| Entry | Base | Time (h), Temp. (°C.) | Volume (mL) | Ratio 21:19 | % Yield 1 |
|---|---|---|---|---|---|
| 1 | NaHCO$_3$ | 48,100 | 10 | 3:1 | 27 |
| 2 | NaHCO$_3$ | 72,100 | 5 | 3:1 | 52 |
| 3 | NaHCO$_3$ | 72,100 | 2.5 | 3:1 | 46 |

The effect of base was also studied. The results are summarized in Table 3, which demonstrate that NaHCO$_3$, Et$_3$N, and Na$_2$CO$_3$ work almost equally well to assist the reaction.

TABLE 3

Effect of Base

| Entry | Base | Time (h), Temp. (°C.) | Volume (mL) | Ratio 21:19 | % Yield 1 |
|---|---|---|---|---|---|
| 1 | KOAc | 72,100 | 5 | 3:1 | 34 |
| 2 | Na$_2$CO$_3$ | 72,100 | 5 | 3:1 | 45 |
| 3 | NaHCO$_3$ | 72,100 | 5 | 3:1 | 52* |
| 4 | NaOAc | 72,100 | 5 | 3:1 | 33 |
| 5 | K$_2$CO$_3$ | 72,100 | 5 | 3:1 | 43 |
| 6 | KHCO$_3$ | 72,100 | 5 | 3:1 | 38 |
| 7 | Et$_3$N | 72,100 | 5 | 3:1 | 45 |
| 8 | Li$_2$CO$_3$ | 72,100 | 5 | 3:1 | 4 |
| 9 | LiOAc | 72,100 | 5 | 3:1 | 40 |

*Isolated yield and optimal conditions.

One trial was performed by switching the ratio of benzopyran and o-iodophenol, the results are presented in Table 4. It was found that both reactions gave nearly identical results. Based on this result and the fact that any unreacted phenol could be easily removed upon work-up, o-iodophenol was used in excess.

TABLE 4

Effect of Ratio

| Entry | Base | Time (h), Temp. (°C.) | Volume (mL) | Ratio 21:19 | % Yield 1 |
|---|---|---|---|---|---|
| 1 | NaHCO$_3$ | 72,100 | 5 | 3:1 | 52 |
| 2 | NaHCO$_3$ | 72,100 | 5 | 1:3 | 54 |

The reaction with various benzopyrans and iodophenols was investigated. Table 5 summarizes the results for the annulation of a variety of benzopyrans with iodophenols using our standard procedure. As noted in Table 5, this methodology is well suited for the synthesis of pterocarpan derivatives in fair to good yields. The reaction utilizing 4-acetyl-2-iodophenol gives a higher yield (entry 2) than that using o-iodophenol as the starting material (entry 1) under otherwise identical reaction conditions. This suggests that an electron-withdrawing group on the aryl halide facilitates the reaction. The electron-withdrawing group may facilitate the oxidative-addition of the carbonhalide bond to palladium. Some polar unidentified by-products were also formed in small amounts along with the pterocarpans.

TABLE 5

Palladium-Catalyzed Annulation of Benzopyrans by o-Iodophenols

| Entry/ Ex. | benzopyran (formula II) | | aryl halide (formula III) | | | yield of product (formula I) |
|---|---|---|---|---|---|---|
| | R$_1$ | R$_4$ | X | R$_2$ | R$_3$ | |
| 1/II | H | H | I | H | H | 54 (1)* |
| 2/III | H | H | I | Ac | H | 64 (24) |
| 3/IV | CH$_3$O | H | I | H | H | 40 (26) |
| 4/V | CH$_3$O | H | I | Ac | H | 53 (27) |
| 5/VI | H | CH$_3$ | I | Ac | H | 31 (28) |
| 6/VII | H | Ph | I | Ac | H | 36 (29) |
| 7/VIII | H | CH$_3$ | I | CHO | CH$_3$O | 34 (30) |

*(compound number)

The stereochemistry of the ring junction in all of the pterocarpans was determined to be cis by comparison of the $^1$H NMR spectral data with that of related compounds reported in the literature (Engler et al., *J. Org. Chem.*, 1990, 55, 1248; Engler et al., *J. Am. Chem. Soc.*, 1991, 113, 5068; Engler et at., *Bioorg. Med. Lett*, 1993, 3, 1229). The cis-stereochemistry of 28 was confirmed by a 2D NOESY spectrum which demonstrated that the palladium addition proceeded through addition to the less hindered face of the carbon-carbon double bond. This approach is much more versatile than the Engler's quirtone-based process (Engler et al., *J. Org. Chem.*, 1990, 55, 1248; Engler et al., *J. Am. Chem. Soc.*, 1991, 113, 5068; Engler et al., *Bioorg, Med. Lett*, 1993, 3, 1229), which necessarily puts an oxygen-substituent in the 8-position of the pterocarpan.

The following examples are intended to illustrate, but not limit, the invention.

EXAMPLES

General-Equipment: All $^1$H NMR and $^{13}$C NMR spectra were recorded at 300 and 75.5 MHz, respectively. Thin-layer chromatography (TLC) was performed using commercially prepared 60-mesh silica gel plates (Whatman K6F), and visualization was effected with short wavelength UV light (254 nm). Infrared spectra were obtained on an IBM IR/98

FT-IR. High-resolution mass spectra (HRMS) were obtained on a VG Instruments ZAB double-focusing mass spectrometer. Melting points were obtained on a Mel-Temp apparatus and are uncorrected.

Solvents and Reagents: All reagents were used directly as received commercially unless otherwise noted. All palladium compounds were donated by Johnson Matthey, Inc. and Kawaken Fine Chemicals Co., Ltd. o-Iodophenol was purchased from Lancaster Co. N,N-Dimethylformamide and dimethylsulfoxide were purchased from Aldrich and used without further purification.

General procedure for the palladium-catalyzed preparation of pterocarpans: To a 10 mL round bottom flask are added the $Pd(OAc)_2$ (0.025 mmol, 5 mol %, 5.6 mg), the o-iodophenol (1.5 mmol), abase (1.75 mmol), tetra-n-butylammonium chloride (0.5 mmol), DMF (5 ml), and 2H-benzopyran (0.5 mmol, 66 mg). The flask is flushed with $N_2$ and then protected under a $N_2$ balloon. After heating at 100° C. for 3 days, the reaction mixture is diluted with ether and washed with 10% NaOH, saturated $NH_4Cl$, and $H_2O$. The organic layer was dried over $MgSO_4$, concentrated, and purified by flash column chromatography (15: 1 hexanes/ ethyl acetate). Crystallization of the product from hexane gave pterocarpan as colorless needles.

Example I—6a,11a-cis-Dihydro-6H-benzofuro[3,2-c] benzopyran (1) (Horino et al., *J. Chem. Soc., Chem. Commun.*, 1976, 500) was obtained as a colorless crystal in 54% yield: mp 125°–6° C. [literature (Harper et al., *J. Chem. Soc., Chem. Commun.*, 1965, 309): 125°–7° C.]; $^1$H NMR $(CDCl_3)\delta 3.67$ (m, 2H), 4.29 (m, 1H), 5.53 (d, J=6.3 Hz, 1H), 6.85–7.57 (m, 8H); $^{13}$C NMR $(CDCl_3)\delta 40.33$, 66.32, 77.58, 110.17, 117.41, 119.97, 120.93, 121.71, 124.69, 127.02, 129.19, 130.03, 131.07, 155.43, 159.25; IR $(CDCl_3)$ 2980, 2894, 1584, 1487, 1457, 1342, 1255, 1229, 931, 753 $cm^{-1}$; HRMS m/z 224.0834 (calcd for $C_{15}H_{12}O_2$, 224.0837).

Example II—8-Acetyl-6a,11a-cis-dihydro-6H-benzofuro [3,2-c]benzopyran (24) was obtained as a white crystalline solid in 64% yield: mp 118°–120° C.; $^1$H NMR $(CDCl_3)$ $\delta 2.55$ (s, 3H), 3.70 (m, 2H), 4.31 (m, 1H), 5.64 (d, J=6.9 Hz, 1H), 6.85 (d, J=8.4 Hz, 1H), 6.94 (d, J=8.4 Hz, 1H), 7.05 (t, J=7.5 Hz, 1H), 7.28 (t, J=7.5 Hz, 1H), 7.52 (d, J=7.2 Hz, 1H), 7.84 (dd, J=8.4, 1.8 Hz, 1H), 7.92 (s, 1H); $^{13}$C NMR $(CDCl_3)\delta 26.37$, 39.78, 66.05, 78.87, 109.64, 117.47, 119.31, 121.84, 125.20, 127.82, 130.26, 130.88, 131.06, 131.41, 155.40, 163.36, 196.29; IR $(CDCl_3)$2980, 2872, 2253, 1673 (C=O), 1610, 1489, 1253, 909, 737 $cm^{-1}$; HRMS m/z 266.0944 (calcd for $C_{17}H_{14}O_3$, 266.0943).

Example III—3-Methoxy-6a,11a-cis-dihydro-6H-benzofuro[3,2-c]benzopyran (26) was obtained as a white crystalline solid in 40% yield: mp 89°–91° C.; $^1$H NMR $(CDCl_3)\delta 3.69$ (m, 2H), 3.78 (s, 3H), 4.27 (m, 1H), 5.49 (d, J=6.6 Hz, 1H), 6.46 (d, J=2.4 Hz, 1H), 6.64 (dd, J=8.4, 2.4 Hz, 1H), 6.87 (m, 2H), 7.18 (m, 2H), 7.43 (d, J=8.7 Hz, 1H); $^{13}$C NMR $(CDCl_3)\delta 40.11$, 55.33, 66.32, 77.65, 101.59, 109.16, 110.14, 112.20, 120.78, 124.66, 127.08, 129.13, 131.84, 156.50, 159.29, 160.97, 160.97; IR $(CDCl_3)$ 2980, 2894, 2360, 2252, 1620, 1475, 1224, 1169, 908, 732 $cm^{-1}$; HRMS m/z 254.0940 (calcd for $C_{16}H_{14}O_3$, 254.0943).

Example IV—8-Acetyl-3-methoxy-6a,11a-cis-dihydro-6H-benzofuro[3,2-c]benzopyran (27) was obtained as a white crystalline solid in 53% yield: mp 123°–126° C.; $^1$H NMR $(CDCl_3)\delta 2.56$ (s, 3H), 3.70 (m, 2H), 3.79 (s, 3H), 4.31 (m, 1H), 5.62 (d, J=6.3 Hz, 1H), 6.46 (d, J=2.4 Hz, 1H), 6.65 (dd, J=8.7, 2.7 Hz, 1H), 6.85 (d, J=8.4 Hz, 1H), 7.41 (d, J=8.4 Hz, 1H), 7.85 (dd, J=8.4, 1.8 Hz, 1H), 7.92 (s, 1H); $^{13}$C NMR $(CDCl_3)\delta 26.39$, 39.63, 55.35, 66.13, 79.10, 101.63, 109.40, 109.67, 111.56, 125.21, 127.96, 131.00, 131.72, 156.60, 161.16, 163.51, 196.35; IR $(CDCl_3)$ 2980, 2894, 2360, 1673 (C=O), 1609, 1586, 1488, 1230, 1194 $cm^{-1}$; HRMS m/z 296.1056 (calcd for $C_{18}H_{16}O_4$, 296.1049).

Example V—8-Acetyl-6-methyl-6a,11a-cis-dihydro-6H-benzofuro[3,2-c]benzopyran (28) was obtained as a white crystalline solid in 31% yield: mp 174°–175 ° C.; $^1$H NMR $(CDCl_3)\delta 1.55$ (d, J=6.3 Hz, 3H), 2.58 (s, 3H), 3.24 (dd, J=10.8, 6.9 Hz, 1H), 3.66 (dd, d=10.8, 6.3 Hz, 1H), 5.58 (d, J=6.6 Hz, 1H), 6.88–7.98 (m, 7H); $^{13}$C NMR $(CDCl_3)$ $\delta 18.01$, 26.42, 46.12, 72.11, 79.90, 109.64, 117.37, 118.86, 121.61, 126.35, 128.50, 130.28, 130.51, 130.96, 131.46, 155.23, 163.45, 196.29; IR $(CDCl_3)$ 2980, 2894, 2360, 2253, 1674 (C=O), 1609, 1488, 1249, 1117, 910, 730 $cm^{-1}$; HRMS m/z 280.1098 (calcd for $C_{18}H_{16}O_3$, 280.1099).

Example VI—8-Acetyl-6-phenyl-6a,11a-cis-dihydro-6H-benzofuro(3,2-c)benzopyran (29) was obtained as a white crystalline solid in 36% yield: mp 198.5°–199.5° C.; $^1$H NMR $(CDCl_3)\delta 2.31$ (s, 3H), 3.63 (dd, J=10.8, 6.9 Hz, 1H), 4.43 (d, J=11.1 Hz, 1H), 5.70 (d, J=6.9 Hz, 1H), 6.83–7.75 (m, 10 H), 7.63 (dd, J=7.8, 1.5 Hz, 1H), 7.86 (dd, J=8.4, 1.8 Hz, 1H); $^{13}$C NMR $(CDCl_3)\delta 26.22$, 46.53, 78.99, 80.02, 109.79, 117.78, 118.95, 122.02, 127.10, 127.46, 128.11, 128.52, 129.14, 130.41, 130.50, 130.63, 130.96, 137.14, 155.51, 163.41, 196.12; IR $(CDCl_3)$ 2980, 2894, 2360, 2253, 1683 (C=O), 1611, 1590, 1489, 1360, 1286, 1239, 907, 732 $cm^{-1}$; HRMS m/z 342.1263 (calcd for $C_{23}H_{18}O_3$, 342.1256).

Example VII—8-Formyl-10-methoxy-6-methyl-6a,11a-cis-dihydro-6H-benzofuro[3,2-c]benzopyran (30) was obtained as a white crystalline solid in 34% yield: mp 165°–166° C.; $^1$H NMR $(CDCl_3)\delta 1.55$ (d, J=6.3 Hz, 3H), 3.28 (dd, J=10.5, 6.6 Hz, 1H), 3.71 (m, 1H), 3.95 (s, 3H), 5.67 (d, J=6.9 Hz, 1H), 6.97 (d, J=8.1 Hz, 1H), 7.05 (t, J=7.2 Hz, 1H), 7.30 (t, J=6.9 Hz, 1H), 7.40 (s, 1H), 7.48 (s, 1H), 7.63 (dd, J=7.5, 1.2 Hz, 1H), 9.86 (s, 1H); $^{13}$C NMR $(CDCl_3)\delta 18.04$, 46.36, 56.02, 71.96, 80.87, 112.34, 117.16, 118.39, 121.53, 121.83, 129.25, 130.33, 130.83, 131.26, 145.27, 153.50, 155.11, 190.20; IR $(CDCl_3)$ 2980, 2894, 2803, 2253, 1687 (C=O), 1609, 1588, 1490, 1463, 1342, 1302, 1223, 1136, 1082, 909, 732 $cm^{-1}$; HRMS m/z 296.1049 (calcd for $C_{18}H_{16}O_4$, 296.1049).

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method of synthesizing a compound of formula (I):

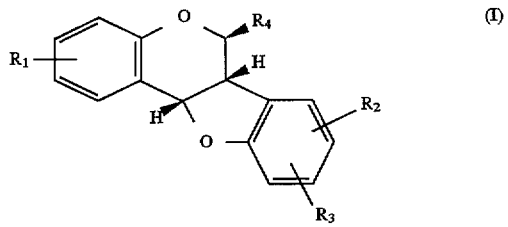

wherein $R_1$ and $R_3$ are independently H, hydroxyl, $(C_1-C_4)$ alkyl or $(C_1-C_4)$alkoxy;

$R_2$ is $R_5C(O)$— where $R_5$ is $(C_1-C_4)$alkyl or H; and $R_4$ is H, $(C_1-C_4)$alkyl or $(C_5-C_7)$aryl optionally substituted with halo, $(C_1-C_4)$alkyl or halo;

comprising reacting a compound of formula (II):

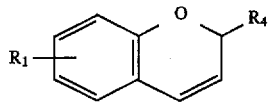
(II)

with a compound of formula (III):

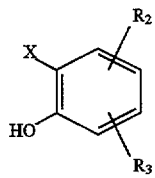
(III)

where X is halo;
in the presence of a catalytic amount of a Pd catalyst.

2. The method of claim 1 wherein $R_1$, $R_2$, $R_3$ and $R_4$ are H.

3. The method of claim 1 wherein $R_2$ is $CH_3C(O)$—.

4. The method of claim 3 wherein $R_1$, $R_3$ and $R_4$ are H.

5. The method of claim 3 wherein $R_1$ is $CH_3O$— and $R_3$ and $R_4$ are H.

6. The method of claim 3 wherein $R_1$ and $R_3$ are H and $R_4$ is $CH_3$.

7. The method of claim 3 wherein $R_1$ and $R_3$ are H and $R_4$ is phenyl.

8. The method of claim 1 wherein $R_1$ is $CH_3O$— and $R_2$, $R_3$ and $R_4$ are H.

9. The method of claim 1 wherein $R_1$ is H, $R_2$ is $CH(O)$—, $R_3$ is —$OCH_3$ and $R_4$ is $CH_3$.

10. The method of claim 1 wherein X is I.

11. The method of claim 1 wherein the Pd catalyst is a Pd(0) catalyst.

12. The method of claim 11 wherein the Pd(0) catalyst is $Pd(OAc)_2$.

13. The method of claim 1 wherein the compound of formula (II) is reacted with the compound of formula (III) in the presence of a base and a chloride ion source.

14. The method of claim 13 wherein the base is $NaHCO_3$, $NEt_3$ or $Na_2CO_3$.

15. The method of claim 13 wherein the chloride ion source is n-$Bu_4NCl$.

16. The method of claim 13 wherein the ratio of base to the compound of formula (II) is about 3.5:1.

* * * * *